US010194645B2

(12) United States Patent
Brüggemann et al.

(10) Patent No.: US 10,194,645 B2
(45) Date of Patent: *Feb. 5, 2019

(54) MOUSE λ LIGHT CHAIN LOCUS

(71) Applicant: Crescendo Biologics Limited, Cambridge (GB)

(72) Inventors: Marianne Brüggemann, Cambridge (GB); Xiangang Zou, Cambridge (GB)

(73) Assignee: Crescendo Biologics Limited, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/230,564

(22) Filed: Aug. 8, 2016

(65) Prior Publication Data

US 2017/0049083 A1    Feb. 23, 2017

Related U.S. Application Data

(63) Continuation of application No. 13/654,007, filed on Oct. 17, 2012, now Pat. No. 9,439,405, which is a continuation of application No. 12/476,087, filed on Jun. 1, 2009, now Pat. No. 8,367,888, which is a continuation of application No. 10/481,395, filed as application No. PCT/GB02/02867 on Jun. 21, 2002, now Pat. No. 7,541,513.

(51) Int. Cl.
| | |
|---|---|
| *A01K 67/027* | (2006.01) |
| *A01K 67/00* | (2006.01) |
| *C07K 16/00* | (2006.01) |
| *C07K 16/06* | (2006.01) |

(52) U.S. Cl.
CPC .......... *A01K 67/0276* (2013.01); *C07K 16/00* (2013.01); *C07K 16/06* (2013.01); *A01K 2217/058* (2013.01); *A01K 2217/075* (2013.01); *A01K 2227/105* (2013.01); *A01K 2267/01* (2013.01); *C07K 2317/56* (2013.01); *C12N 2800/30* (2013.01)

(58) Field of Classification Search
CPC .......... A01K 67/0278; A01K 2227/105; A01K 2267/01; A01K 2207/15; A01K 2217/05; A01K 2217/075; A01K 67/0276; C07K 16/00; C07K 2317/22; C07K 2317/569
USPC .................................................... 800/18, 13
See application file for complete search history.

(56) References Cited

U.S. PATENT DOCUMENTS

| | | | |
|---|---|---|---|
| 5,770,429 A | 6/1998 | Lonberg et al. | |
| 6,162,963 A | 12/2000 | Kucherlapati et al. | |
| 7,541,513 B2* | 6/2009 | Bruggeman ....... | A01K 67/0276 800/21 |
| 8,367,888 B2* | 2/2013 | Bruggemann ..... | A01K 67/0276 800/18 |
| 9,439,405 B2* | 9/2016 | Bruggemann ..... | A01K 67/0276 |

FOREIGN PATENT DOCUMENTS

| | | |
|---|---|---|
| EP | 1399559 | 3/2004 |
| WO | WO 1990/004036 | 4/1990 |
| WO | WO 1994/002602 | 2/1994 |
| WO | WO 1996/033735 | 10/1996 |
| WO | WO 98/24884 * | 6/1998 |
| WO | WO 2000/026373 | 5/2000 |
| WO | WO 2002/012437 A2 | 2/2002 |
| WO | WO 2002/066630 | 8/2002 |
| WO | WO 2002/085944 A2 | 10/2002 |
| WO | WO 2002/085945 A2 | 10/2002 |
| WO | WO 2003/002609 A2 | 1/2003 |
| WO | WO 2004/049794 A2 | 6/2004 |

OTHER PUBLICATIONS

Declaration under 37 CFR 1.132 by Simon Andrews, signed Nov. 17, 2011, and submitted in parent U.S. Appl. No. 12/476,087.*
Board of Appeal Decision in appeal T1526/11-3.3.08 of decision of Opposition Division in EP 1399559 (EP 02732970.5), dated Mar. 17, 2015. 22 pages.
Declaration and Curriculum Vitae of Andrei V. Popov, Ph.D. filed in EP 02732970.5, dated Feb. 3, 2011. 7 pages.
Declaration and Curriculum Vitae of Andrei V. Popov, Ph.D. filed in U.S. Appl. No. 12/476,087, dated Nov. 16, 2011. 14 pages.
Declaration and Curriculum Vitae of Anne E. Corcoran, Ph.D. filed in opposition against EP 1776383, dated May 15, 2015. 13 pages.
Declaration and Curriculum Vitae of Daniel Corcos, MD, Ph.D. filed in opposition against EP 1776383, dated May 20, 2015. 18 pages.
Declaration and Curriculum Vitae of Lutz Riechmann, Ph.D. filed in opposition against EP 1776383, dated May 20, 2015. 40 pages.
Declaration and Curriculum Vitae of Michael R. Clark, Ph.D. filed in opposition against EP 1776383, dated May 18, 2015. 30 pages.
Declaration and Curriculum Vitae of Xiangang Zou, Ph.D. filed in EP 02732970.5, dated Feb. 3, 2011. 6 pages.
Declaration by Dr. Anton Berns. Mar. 3, 2011.
Declaration by Professor Montoliu.
Declaration by Professor Peterson.
Declaration by Vivek Iyer.
Declaration of Dr. Simon Andrews. Mar. 2, 2011.
Declaration of Marianne Bruggemann, Ph.D. submitted in U.S. Appl. No. 10/481,395, dated Mar. 6, 2007. 3 pages.

(Continued)

*Primary Examiner* — Anne Marie S Wehbe
(74) *Attorney, Agent, or Firm* — Wolf, Greenfield & Sacks, P.C.

(57) ABSTRACT

The present invention provides in a first aspect a mouse in which the λ (lambda) light chain locus has been functionally silenced. In one embodiment, the mouse λ light chain locus was functional silenced by deletion of gene segments coding for the λ light chain locus. In a further aspect, a mouse containing functionally silenced λ and κ (kappa) L chain loci was produced. The invention is useful for the production of antibodies, for example heterologous antibodies, including heavy chain only antibodies.

7 Claims, 6 Drawing Sheets

Specification includes a Sequence Listing.

(56) References Cited

OTHER PUBLICATIONS

Declaration of Rudi W. Hendriks, Ph.D. filed in EP 02732970.5, dated Nov. 22, 2010. 6 pages.
Declaration of Ton Logtenberg. Mar. 3, 2011.
EPO communication pursuant to Rule 82(2) in connection with EP 02732970.5, dated Apr. 28, 2015. 18 pages.
Notice of Opposition to a European Patent—Harbour Antibodies B.V. Jan. 28, 2009.
Notice of Opposition to a European Patent—John Gerard Leeming. Jan. 29, 2009.
Notice of Opposition to a European Patent—Merus B.V. Jan. 30, 2009.
Opposition by Crescendo Biologics Limited to European Patent No. EP 1776383. 46 pages.
Opposition Division Decision in connection with EP 02732970.5, dated May 10, 2011. 22 pages.
Priority document for GB 0115256.0. Jun. 21, 2001.
Statement by Dr. Andrei Popov. Dec. 2, 2009.
[No Author Listed] Report submitted by Opponent 3 filed in EP 02732970.5 on Dec. 2, 2010 entitled "Description of MuVλ-KO project P07078-R14" 6 pages.
Alexander et al., gamma Heavy chain disease in man: cDNA sequence supports partial gene deletion model. Proc Natl Acad Sci U S A. May 1982;79(10):3260-4.
Araki et al., Efficiency of recombination by Cre transient expression in embryonic stem cells: comparison of various promoters. J Biochem. Nov. 1997;122(5):977-82.
Arbabi Ghahroudi et al., Selection and identification of single domain antibody fragments from camel heavy-chain antibodies. FEBS Lett. Sep. 15, 1997;414(3):521-6.
Barthelemy et al., Comprehensive analysis of the factors contributing to the stability and solubility of autonomous human VH domains. J Biol Chem. Feb. 8, 2008;283(6):3639-54. Epub Nov. 28, 2007.
Bedell et al., Mouse models of human disease. Part I: techniques and resources for genetic analysis in mice. Genes Dev. Jan. 1, 1997;11(1):1-10.
Bell et al., A selective defect in IgM antigen receptor synthesis and transport causes loss of cell surface IgM expression on tolerant B lymphocytes. EMBO J. Feb. 15, 1994;13(4):816-26.
Blomberg et al., Organization of four mouse lambda light chain immunoglobulin genes. Proc Natl Acad Sci U S A. Jun. 1981;78(6):3765-9.
Boder et al., Yeast surface display for screening combinatorial polypeptide libraries. Nat Biotechnol. Jun. 1997;15(6):553-7.
Bond et al., A structure-based database of antibody variable domain diversity. J Mol Biol. May 6, 2005;348(3):699-709.
Bossy et al., Organization and expression of the lambda-like genes that contribute to the mu-psi light chain complex in human pre-B cells. Int Immunol. Nov. 1991;3(11):1081-90.
Boudinot et al., Conserved distribution of lambda subtypes from rearranged gene segments to immunoglobulin synthesis in the mouse B cell repertoire. Eur J Immunol. Sep. 1994;24(9):2013-7.
Bruggemann et al., A repertoire of monoclonal antibodies with human heavy chains from transgenic mice. Proc Natl Acad Sci U S A. Sep. 1989;86(17):6709-13.
Bruggemann, Human antibody expression in transgenic mice. Arch Immunol Ther Exp (Warsz). 2001;49(3):203-8.
Butler, Immunoglobulin diversity, B-cell and antibody repertoire development in large farm animals. Rev Sci Tech. Apr. 1998;17(1):43-70.
Cai et al., A melanoma-specific VH antibody cloned from a fusion phage library of a vaccinated melanoma patient. Proc Natl Acad Sci U S A. Jun. 25, 1996;93(13):6280-5.
Cai et al., Comparison of fusion phage libraries displaying VH or single-chain Fv antibody fragments derived from the antibody repertoire of a vaccinated melanoma patient as a source of melanoma-specific targeting molecules. Proc Natl Acad Sci U S A. Aug. 19, 1997;94(17):9261-6.

Carson et al., A linkage map of the mouse immunoglobulin lambda light chain locus. Immunogenetics. 1989;29(3):173-9.
Chen et al., B cell development in mice that lack one or both immunoglobulin kappa light chain genes. EMBO J. Mar. 1993;12(3):821-30.
Chen et al., Immunoglobulin gene rearrangement in B cell deficient mice generated by targeted deletion of the JH locus. Int Immunol. Jun. 1993;5(6):647-56.
Cheng et al., Syk tyrosine kinase required for mouse viability and B-cell development. Nature. Nov. 16, 1995;378(6554):303-6.
Collins et al., A mouse for all reasons. A mouse for all reasons.
Corcos et al., Pre-B-cell development in the absence of lambda 5 in transgenic mice expressing a heavy-chain disease protein. Curr Biol. Oct. 1, 1995;5(10):1140-8.
Cowan et al., Purification and Sequence of the mRNA Coding for an Immunoglobulin Heavy Chain. Eur. J. Biochem. 1976;61:355-368.
Davies et al., 'Camelising' human antibody fragments: NMR studies on VH domains. FEBS Lett. Feb. 21, 1994;339(3):285-90.
Davies et al., Antibody VH domains as small recognition units. Biotechnol May 1995;13(5):475-9.
Davies et al., Single antibody domains as small recognition units: design and in vitro antigen selection of camelized, human VH domains with improved protein stability. Protein Eng. Jun. 1996;9(6):531-7.
Decanniere et al., A single-domain antibody fragment in complex with RNase A: non-canonical loop structures and nanomolar affinity using two CDR loops. Structure 1993. Apr. 15, 1999;7(4):361-70.
Deng et al., Location of Crossovers during Gene Targeting with Insertion and Replacement Vectors. Mol Cell Biol 1993 13(4):2134-40.
Deng et al., Reexamination of gene targeting frequency as a function of the extent of homology between the targeting vector and the target locus. Mol Cell Biol. Aug. 1992;12(8):3365-71.
Desmyter et al., et al. Crystal structure of a camel single-domain VH antibody fragment in complex with lysozyme. Nat Struct Biol. Sep. 1996;3(9):803-11.
Disanto et al., Lymphoid development in mice with a targeted deletion of the interleukin 2 receptor gamma chain. Proc Natl Acad Sci U S A. Jan. 17, 1995;92(2):377-81.
Donohoe et al., Transgenic human lambda 5 rescues the murine lambda 5 nullizygous phenotype. J Immunol. May 15, 2000;164(10):5269-76.
Dunnick et al., Switch recombination and somatic hypermutation are controlled by the heavy chain 3' enhancer region. J Exp Med. Nov. 23, 2009;206(12):2613-23. doi: 10.1084/jem.20091280.
Echelard, Year of the ox. Nat Biotechnol. Feb. 2009;27(2):146-7.
Ehlich et al., Immunoglobulin heavy and light chain genes rearrange independently at early stages of B cell development. Cell. Mar. 12, 1993;72(5):695-704.
Eisen et al., Lambda chains and genes in inbred mice. Annu Rev Immunol. 1985;3:337-65.
Fruman et al., Impaired B cell development and proliferation in absence of phosphoinositide 3-kinase p85alpha. Science. Jan. 15, 1999;283(5400):393-7.
Galler et al., Surface mu heavy chain signals down-regulation of the V(D)J-recombinase machinery in the absence of surrogate light chain components. J Exp Med. Jun. 7, 2004;199(11):1523-32.
Glaser et al., Current issues in mouse genome engineering. Nat Genet. Nov. 2005;37(11):1187-93.
Goldstein, Laskers for 2001: knockout mice and test-tube babies. Nat Med. Oct. 2001;7(10):1079-80.
Gollahon et al., Ig lambda-producing B cells do not show feedback inhibition of gene rearrangement. J Immunol. Oct. 15, 1988;141(8):2771-80.
Gong et al., Regulation of an early developmental checkpoint in the B cell pathway by Ig beta. Science. Apr. 19, 1996;272(5260):411-4.
Green Antibody engineering via genetic engineering of the mouse: XenoMouse strains are a vehicle for the facile generation of therapeutic human monoclonal antibodies. J Immunol Methods. Dec. 10, 1999;231(1-2):11-23.

(56) References Cited

OTHER PUBLICATIONS

Green et al., Antigen-specific human monoclonal antibodies from mice engineered with human Ig heavy chain and light chain YACs. Nat Genet. May 1994;7(1):13-21.
Gu et al., Independent control of immunoglobulin switch recombination at individual switch regions evidenced through Cre-loxP-mediated gene targeting. Cell. Jun. 18, 1993;73(6):1155-64.
Hamers-Casterman et al., Naturally occurring antibodies devoid of light chains. Nature. Jun. 3, 1993;363(6428):446-8.
Harmsen et al., Llama heavy-chain V regions consist of at least four distinct subfamilies revealing novel sequence features. Mol Immunol. Aug. 2000;37(10):579-90.
Hasan et al., Incomplete block of B cell development and immunoglobulin production in mice carrying the muMT mutation on the BALB/c background. Eur J Immunol. Dec. 2002;32(12):3463-71.
Hasty et al., The length of homology required for gene targeting in embryonic stem cells. Mol Cell Biol. Nov. 1991;11(11):5586-91.
He et al., Tissue-specific targeting of the pthrp gene: the generation of mice with floxed alleles. Endocrinology. May 2001;142(5):2070-7.
Hendershot et al., Assembly and secretion of heavy chains that do not associate posttranslationally with immunoglobulin heavy chain binding protein. J. Cell. Biol. 104: 761-767, 1987.
Hogan et al., In: Manipulating the mouse embryo, section E. a laboratory manual. Cold Spring Harbor Laboratory Press. 1994;217-251.
Hogan et al., In: Manipulating the mouse embryo, section F. a laboratory manual. Cold Spring Harbor Laboratory Press. 1994;253-289.
Holt et al., Domain antibodies: proteins for therapy. Trends Biotechnol. Nov. 2003;21(11):484-90.
Houdebine, Transgenic animal bioreactors. Transgenic Res. 2000;9(4-5):305-20.
Hunt et al., Rapid molecular weight estimation and separation of selected immunoglobulin chains by high speed gel filtration. J Immunol Methods. Dec. 16, 1983;65(1-2):199-205.
Janssens et al., Generation of heavy-chain-only antibodies in mice. Proc Natl Acad Sci U S A. Oct. 10, 2006;103(41):15130-5.
Jiang et al., Gene targeting: things go better with Cre. Curr Biol. May 1, 1997;7(5):R321-3.
Joyner, Gene Targeting: a practical approach. Oxford University Press. 2$^{nd}$ edition. Cover and Table of Contents. 2000.
Kellermann et al., Antibody discovery: the use of transgenic mice to generate human monoclonal antibodies for therapeutics. Curr Opin Biotechnol. Dec. 2002;13(6):593-7.
Kitamura et al., A B cell-deficient mouse by targeted disruption of the membrane exon of the immunoglobulin mu chain gene. Nature. Apr. 4, 1991;350(6317):423-6.
Kitamura et al., A critical role of lambda 5 protein in B cell development. Cell. May 29, 1992;69(5):823-31.
Kitamura et al., Targeted disruption of mu chain membrane exon causes loss of heavy-chain allelic exclusion. Nature. Mar. 12, 1992;356(6365):154-6.
Kolb et al., Insertion of a foreign gene into the beta-casein locus by Cre-mediated site-specific recombination. Gene. Feb. 4, 1999;227(1):21-31.
Kühn et al., Advances in gene targeting methods. Curr Opin Immunol. Apr. 1997;9(2):183-8.
Kuroiwa et al., Cloned transchromosomic calves producing human immunoglobulin. Nat Biotechnol. Sep. 2002;20(9):889-94.
Lariviere et al., Transgenic studies of pain and analgesia: mutation or background genotype? J Pharmacol Exp Ther. May 2001;297(2):467-73.
Leiter, Mice with targeted gene disruptions or gene insertions for diabetes research: problems, pitfalls, and potential solutions. Diabetologia. Mar. 2002;45(3):296-308.
Lepage et al., Rapid generation of nested chromosomal deletions on mouse chromosome 2. Proc Natl Acad Sci U S A. Sep. 12, 2000;97(19):10471-6.
Li et al., Generation of mice with a 200-kb amyloid precursor protein gene deletion by Cre recombinase-mediated site-specific recombination in embryonic stem cells. Proc Natl Acad Sci U S A. Jun. 11, 1996;93(12):6158-62. Erratum in: Proc Natl Acad Sci U S A Oct. 15, 1996;93(21):12052.
Liu et al., Embryonic lethality and tumorigenesis caused by segmental aneuploidy on mouse chromosome 11. Genetics. Nov. 1998;150(3):1155-68.
Lonberg et al. Antigen-specific human antibodies from mice comprising four distinct genetic modifications. Nature 368,856-859,1994.
Lonberg Human antibodies from transgenic animals. Nat Biotechnol. Sep. 2005;23(9):1117-25.
MacPherson et al., BLySsful interactions between DCs and B cells. Nat Immunol. Sep. 2002;3(9):798-800.
MacPherson et al., IgA production without mu or delta chain expression in developing B cells. Nat Immunol. Jul. 2001;2(7):625-31.
Madsen et al., Mice lacking all conventional MHC class II genes. Proc Natl Acad Sci U S A. Aug. 31, 1999;96(18):10338-43.
Manis et al., Class switching in B cells lacking 3' immunoglobulin heavy chain enhancers. J Exp Med. Oct. 19, 1998;188(8):1421-31.
March et al., A simplified method for cyanogen bromide activation of agarose for affinity chromatography. Anal Biochem. Jul. 1974;60(1):149-52.
Matheson et al., Light chain-deficient mice produce novel multimeric heavy-chain-only IgA by faulty class switching. Int Immunol. Aug. 2009;21(8):957-66. doi: 10.1093/intimm/dxp062.
Miller et al., Physical linkage of the constant region genes for immunoglobulins lambda I and lambda III. Proc Natl Acad Sci U S A. Jun. 1981;78(6):3829-33.
Miller et al., Structural alterations in J regions of mouse immunoglobulin lambda genes are associated with differential gene expression. Nature. Feb. 4, 1982;295(5848):428-30.
Miller et al.,The order and orientation of mouse lambda-genes explain lambda-rearrangement patterns. J Immunol. Oct. 1, 1988;141(7):2497-502.
Mombaerts et al., RAG-1-deficient mice have no mature B and T lymphocytes. Cell. Mar. 6, 1992;68(5):869-77.
Motoyama et al., Somatic mutation in constant regions of mouse lambda 1 light chains. Proc Natl Acad Sci U S A. Sep. 15, 1991;88(18):7933-7.
Müller, Ten years of gene targeting: targeted mouse mutants, from vector design to phenotype analysis. Mech Dev. Apr. 1999;82(1-2):3-21.
Muyldermans et al., Unique single-domain antigen binding fragments derived from naturally occurring camel heavy-chain antibodies. J Mol Recognit. Apr. 1999;12(2):131-40.
Muyldermans Single domain camel antibodies: current status. J Biotechnol. Jun. 2001;74(4):277-302.
Nagy, Cre recombinase: the universal reagent for genome tailoring. Genesis. Feb. 2000;26(2):99-109.
Nakamura et al., Panning of a phage VH library using nitrocellulose membranes: application to selection of a human VH library. J Biochem. Feb. 2001;129(2):209-12.
Nicholson et al., Antibody repertoires of four- and five-feature translocus mice carrying human immunoglobulin heavy chain and kappa and lambda light chain yeast artificial chromosomes. J Immunol. Dec. 15, 1999;163(12):6898-906.
Nishimoto et al., Normal pre-B cells express a receptor complex of mu heavy chains and surrogate light-chain proteins. Proc Natl Acad Sci U S A. Jul. 15, 1991;88(14):6284-8.
Orinska et al., Novel B cell population producing functional IgG in the absence of membrane IgM expression. Eur J Immunol. Dec.;32(12):3472-80. 2002.
Osoegawa et al., Bacterial artificial chromosome libraries for mouse sequencing and functional analysis. Genome Res. Jan. 2000;10(1):116-28.
Pettitt et al., Agouti C57BL/6N embryonic stem cells for mouse genetic resources. Nat Methods. Jul. 2009;6(7):493-5. doi: 10.1038/nmeth.1342.

(56) References Cited

OTHER PUBLICATIONS

Popov et al., A human immunoglobulin lambda locus is similarly well expressed in mice and humans. J Exp Med. May 17, 1999;189(10):1611-20.
Ramírez-Solis et al., Chromosome engineering in mice. Nature. Dec. 14, 1995;378(6558):720-4.
Reilly et al., Restricted association of V and J-C gene segments for mouse lambda chains. Proc Natl Acad Sci U S A. Apr. 1984;81(8):2484-8.
Reiter et al., An antibody single-domain phage display library of a native heavy chain variable region: isolation of functional single-domain VH molecules with a unique interface. J Mol Biol. Jul. 16, 1999;290(3):685-98.
Ren et al., Silencing of the immunoglobulin heavy chain locus by removal of all eight constant-region genes in a 200-kb region. Genomics. Oct. 2004;84(4):686-95.
Riechmann et al., Single domain antibodies: comparison of camel VH and camelised human VH domains. J Immunol Methods. Dec. 10, 1999;231(1-2):25-38.
Sage et al., Targeted disruption of the three Rb-related genes leads to loss of G(1) control and immortalization. Genes Dev. Dec. 1, 2000;14(23):3037-50.
Sanchez et al., The lambda B cell repertoire of kappa-deficient mice. Int Rev Immunol. 1996;13(4):357-68.
Sauer et al., Cre-stimulated recombination at loxP-containing DNA sequences placed into the mammalian genome. Nucleic Acids Res. Jan. 11, 1989;17(1):147-61.
Sauer et al., Site-specific DNA recombination in mammalian cells by the Cre recombinase of bacteriophage P1. Proc Natl Acad Sci U S A. Jul. 1988;85(14):5166-70.
Sauer et al., Targeted insertion of exogenous DNA into the eukaryotic genome by the Cre recombinase. New Biol. May 1990;2(5):441-9.
Sauer, Inducible gene targeting in mice using the Cre/lox system. Methods. Apr. 1998;14(4):381-92.
Schiff et al., Organization and expression of the pseudo-light chain genes in human B-cell ontogeny. Int Rev Immunol. 1992;8(2-3):135-45.
Schlake et al., Predetermined chromosomal deletion encompassing the Nf-1 gene. Oncogene. Oct. 28, 1999;18(44):6078-82.
Selfridge et al., Gene targeting using a mouse HPRT minigene/HPRT-deficient embryonic stem cell system: inactivation of the mouse ERCC-1 gene. Somat Cell Mol Genet. Jul. 1992;18(4):325-36.
Selsing et al., Evolution of mouse immunoglobulin lambda genes. Proc Natl Acad Sci U S A. Aug. 1982;79(15):4681-5.
Seong et al., To knockout in 129 or in C57BL/6: that is the question. Trends Genet. Feb. 2004;20(2):59-62.
Shinkai et al. RAG-2-deficient mice lack mature lymphocytes owing to inability to initiate V(D)J rearrangement. Cell. Mar. 6. 1992;68(5):855-67.
Sigmund, Viewpoint: are studies in genetically altered mice out of control? Arterioscler Thromb Vasc Biol. Jun. 2000;20(6):1425-9.
Smith et al., A site-directed chromosomal translocation induced in embryonic stem cells by Cre-loxP recombination. Nat Genet. Apr. 1995;9(4):376-85. Erratum in: Nat Genet Jan. 1996;12(1):110.
Stacey et al., Use of double-replacement gene targeting to replace the murine alpha-lactalbumin gene with its human counterpart in embryonic stem cells and mice. Mol Cell Biol. Feb. 1994;14(2):1009-16.
Storb et al., Physical linkage of mouse lambda genes by pulsed-field gel electrophoresis suggests that the rearrangement process favors proximate target sequences. Mol Cell Biol. Feb. 1989;9(2):711-8.
Stricklett et al., The Cre/loxP system and gene targeting in the kidney. Am J Physiol. May 1999;276(5 Pt 2):F651-7.
Sun et al., Insertion of phosphoglycerine kinase (PGK)-neo 5' of Jlambda1 dramatically enhances VJlambda1 rearrangement. J Exp Med. Mar. 19, 2001;193(6):699-712.
Sutherland et al., Cloning and comparative mapping of the DiGeorge syndrome critical region in the mouse. Genomics. Aug. 15, 1998;52(1):37-43.
Tanaka et al., Single domain intracellular antibodies: a minimal fragment for direct in vivo selection of antigen-specific intrabodies. J Mol Biol. Aug. 29, 2003;331(5):1109-20.
Tanha et al., Optimal design features of camelized human single-domain antibody libraries. J Biol Chem. Jul. 6, 2001;276(27):24774-80. Epub May 2, 2001.
Tanha et al., Selection by phage display of llama conventional V(H) fragments with heavy chain antibody V(H)H properties. J Immunol Methods. May 1, 2002;263(1-2):97-109.
Te Riele et al., Highly efficient gene targeting in embryonic stem cells through homologous recombination with isogenic DNA constructs. Proc Natl Acad Sci U S A. Jun. 1, 1992;89(11):5128-32.
Thompson et al., On the relationship of CSF pleocytosis to immunoglobulin levels as estimated by different techniques. J Neuroimmunol. Jun. 1982;2(3-4):321-30.
Torres et al., Laboratory Protocols for conditional gene targeting. Oxford University Press. Cover and Table of Contents. 23-25. 70-71. 1997.
Transue et al., Camel single-domain antibody inhibits enzyme by mimicking carbohydrate substrate. Proteins. Sep. 1, 1998;32(4):515-22.
Turner et al., Perinatal lethality and blocked B-cell development in mice lacking the tyrosine kinase Syk. Nature. Nov. 16, 1995;378(6554):298-302.
Utsumi et al., The Subunits of Purified Rabbit Antibody. Biochemistry. Sep. 1964;3:1329-38.
Van Deursen et al., Cre-mediated site-specific translocation between nonhomologous mouse chromosomes. Proc Natl Acad Sci U S A. Aug. 1, 1995;92(16):7376-80.
Van Spriel et al., Immunotherapeutic perspective for bispecific antibodies. Immunol Today. Aug. 2000;21(8):391-7.
Vasquez et al., Manipulating the mammalian genome by homologous recombination. Proc Natl Acad Sci U S A. Jul. 17, 2001;98(15):8403-10.
Vooijs et al., A highly efficient ligand-regulated Cre recombinase mouse line shows that LoxP recombination is position dependent. EMBO Rep. Apr. 2001;2(4):292-7.
Vu et al., Comparison of llama VH sequences from conventional and heavy chain antibodies. Mol Immunol. Dec. 1997;34(16-17):1121-31.
Ward et al., Binding activities of a repertoire of single immunoglobulin variable domains secreted from *Escherichia coli*. Nature. Oct. 12, 1989;341(6242):544-6.
Weiss et al., Somatic point mutations in unrearranged immunoglobulin gene segments encoding the variable region of lambda light chains. EMBO J. Apr. 1987;6(4):927-32.
Weiss et al., V lambda 2 rearranges with all functional J lambda segments in the mouse. Eur J Immunol. Aug. 1985;15(8):765-8.
Whyatt et al., Introduction of precise alterations into the mouse genome with high efficiency by stable tag-exchange gene targeting: implications for gene targeting in ES cells. Nucleic Acids Res. Jun. 15, 1997;25(12):2381-8.
Wu et al., A protocol for constructing gene targeting vectors: generating knockout mice for the cadherin family and beyond. Nat Protoc.2008;3(6):1056-76.
Wu et al., Length distribution of CDRH3 in antibodies. Proteins. May 1993;16(1):1-7.
Yeung et al., T-cell development and function in gene-knockout mice. Curr Opin Immunol. Apr. 1994;6(2):298-307.
Young et al., Transgenic Res 20: 1139, Abstract 59 (2011).
Zheng et al., Engineering mouse chromosomes with Cre-loxP: range, efficiency, and somatic applications. Mol Cell Biol. Jan. 2000;20(2):648-55.
Zou et al., Block in development at the pre-B-II to immature B cell stage in mice without Ig kappa and Ig lambda light chain. J Immunol. Feb. 1, 2003;170(3):1354-61.
Zou et al., Dominant expression of a 1.3 Mb human Ig kappa locus replacing mouse light chain production. FASEB J. Aug. 1996;10(10):1227-32.
Zou et al., Expression of a dromedary heavy chain-only antibody and B cell development in the mouse. J Immunol. Sep. 15, 2005;175(6):3769-79.

(56) References Cited

OTHER PUBLICATIONS

Zou et al., Gene targeting in the Ig kappa locus: efficient generation of lambda chain-expressing B cells, independent of gene rearrangements in Ig kappa. EMBO J. Mar. 1993;12(3):811-20.
Zou et al., Heavy chain-only antibodies are spontaneously produced in light chain-deficient mice. J Exp Med. Dec. 24, 2007;204(13):3271-83.
Zou et al., Subtle differences in antibody responses and hypermutation of lambda light chains in mice with a disrupted chi constant region. Eur J Immunol. Aug. 1995;25(8):2154-62.
PCT/GB2002/002867, Apr. 29, 2003, International Search Report.
PCT/GB2002/002867, Dec. 2, 2003, International Preliminary Examination Report.

\* cited by examiner

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Synthetic polynucleotide sequence

<400> SEQUENCE: 1
gcctttccca tgctcttgct gtcaggg                                          27

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide sequence

<400> SEQUENCE: 2
ccaagtcttc gccatcagtc accc                                             24

<210> SEQ ID NO 3
<211> LENGTH: 27
<212> TYPE: DNA
<213> ORGANISM: Artificial Sequence
<220> FEATURE:
<223> OTHER INFORMATION: Synthetic polynucleotide sequence

<400> SEQUENCE: 3
cccaggtgct tgccccacag gtttagg                                          27

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide sequence

<400> SEQUENCE: 4
ggagatcagg aatgagggac aaac                                             24

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide sequence

<400> SEQUENCE: 5
ctcgacggat ccgtcgagga attcc                                            25

<210> SEQ ID NO 6
<211> LENGTH: 27
<212> TYPE: DNA
<213> ORGANISM: Artificial Sequence
<220> FEATURE:
<223> OTHER INFORMATION: Synthetic polynucleotide sequence

<400> SEQUENCE: 6
atggccgatc ccatattggc tgcaggg                                          27

MOUSE λ LIGHT CHAIN LOCUS

RELATED APPLICATIONS

This application is a continuation of U.S. application Ser. No. 13/654,007 filed Oct. 17, 2012, which is a continuation of U.S. application Ser. No. 12/476,087 filed Jun. 1, 2009, now U.S. Pat. No. 8,367,888, which is a continuation of U.S. application Ser. No. 10/481,395 filed Feb. 10, 2004, now U.S. Pat. No. 7,541,513, which is a 371 of PCT/GB02/02867 filed Jun. 21, 2002. The entire contents of the above-identified applications are hereby incorporated by reference.

FIELD

The present invention relates to mice in which the λ (lambda) light (L) chain locus and/or the λ and κ (kappa) L chain loci have been functionally silenced, and to antibodies produced by such mice.

BACKGROUND

B-cells express surface immunoglobulin (Ig) either with κ (kappa) or λ L chain, a choice which is termed isotype exclusion. The proportion of antibodies containing a κ or λ L chain varies considerably in the different species but in the mouse only a few percent of antibodies express λ. L chain genes are encoded by 2 different loci, the κ or λ L chain loci, and in the mouse there is an extensive number of V(variable)κ genes upstream of 5 J(joining)κ and 1 C(constant region)κ gene. Although the κ locus is over 10-times larger than the λ locus, with more then 100 V genes, this extensive complexity is not regarded as a reason that most mouse antibodies carry a κ L chain. It may be that the mouse κ locus is simply more efficient in DNA rearrangement which is supported by the finding that in the majority of cells with rearranged Vκ the λ locus is still in germline configuration whilst in most cells expressing λ L chain the κ locus is either non-productively rearranged or deleted.

Several mouse strains with silenced κ L chain locus have been described. They were generated by homologous integration of a selectable marker gene in Cκ or targeted removal of Cκ or Jκ (see for example Zou, X. et al., 1995, Eur. J. Immunol 25(8): 2154-2162).

Silencing expression of κ L chain shed light on isotype exclusion and L chain activation and it was concluded that κ and λ expression are separate and independent events. Although homozygous $\kappa^{-/-}$ mice compensate for the κ deficiency with increased λ production their splenic B-cells and $\mu^+$ cells in the bone marrow can be reduced compared to normal mice. This may suggest that λ L chain rearrangement and expression is perhaps a less efficient process. However, despite the lack of κ L chain these mice are healthy and can mount an efficient immune response.

During B-cell development gene segments encoding Ig H chains rearrange first by D to JH recombination at the pro B-cell stage. This is followed by VH to D-JH recombination at the pre B-I stage and if a μ H chain can pair with a surrogate L chain, consisting of $V_{preB}$ and λ5 protein, this forms a surfaced expressed pre B-cell receptor (pre BCR) at the pre B-II differentiation stage. Cell surface expression of the pre BCR induces proliferation and after several divisions large pre B-II cells differentiate into small resting pre B-II cells. The pre B-II stage with a defined ratio of large and small pre B cells has been identified by surface expression of the IL-2 receptor α chain, CD25. At the transition from pre B-II to immature B cell L chain V-J rearrangement occurs where the surrogate L chain is replaced by κ or λ. At this stage the cells can leave the bone marrow for further differentiation into plasma cells or memory cells in secondary lymphoid organs such as spleen or lymph nodes.

SUMMARY

B-cell development without L chain has not been fully elucidated in the prior art. The BCR consists of two Ig H chains each associated with one Ig L chain in conjunction with the Igα/Igβ coreceptor. These six chains must assemble correctly in the endoplasmic reticulum (ER) to allow transport and cell surface expression of IgM to progress B-cell development. Immature B-cells without L chain are not maintained and a lack of surface IgH, Igα or Igβ expression leads to reduced signal transducer activity which can arrest B-cell maturation. H chain, synthesised prior to L chain, is chaperoned and retained in the cytoplasm but if L chain association fails single H chains, unlike L chains, undergo rapid intracellular degradation as a result of inefficient transported from the ER to the Golgi.

The mouse lambda (δ) light chain locus is about 200 kb in size and comprises 3 variable (V) region genes and 4 joining (J) segments upstream of 4 constant (C) region genes, V2-Vx-J2-C2-J4-C4-V1-J3-C3-J1-C1 (FIG. 1a). Silencing of the δ locus is difficult because homologous integration to delete or disable a single or even two Cδ genes would not be sufficient to prohibit δ light chain rearrangement and expression. To achieve this one would have to disable 2 regions: C2 and C3-C1 which are over 100 kb apart. C4 is regarded a non-functional as no protein has been found. This means two targeting constructs have to be assembled and homologously integrated in the same allele. An advantage would be the use of integrated loxP sites to allow Cre mediated deletion of the whole locus or deletion of relevant functional genes.

There is therefore the need to produce mice in which the δ light chain locus is deleted. It would also be desirable to produce mice lacking functional light chains for the production of heavy chain only antibodies—the exploitation of human antibody-producing mice, for example, is hampered by the problem that mouse lambda L chain associate with a large proportion of the expressed human Ig (or H chain).

According to a first aspect of the present invention, there is provided a mouse in which the λ light chain locus is functionally silenced. A transgenic mouse according to the invention has been produced for the first time by the present inventors. Uses of such a mouse are described below.

The λ light chain locus may be deleted in part or completely. Alternatively, the λ light chain locus may be functionally silenced through deletion of gene segments encoding for the λ light chain locus.

The exemplified procedure of rendering the mouse lambda light chain locus non-functional used two strategies of silencing all constant region genes: 1. integration of a selectable marker gene to disable individual constant region genes and 2. gene and locus deletion. As described further in the Experimental section below, this produced two lambda KO strains, $\lambda 1.3.2^{-/-}\kappa^{-/-}$ and $\lambda 1-2\Delta^{-/-}\kappa^{-/-}$ mice, with essentially the same features of a silent lambda locus. Silencing of the mouse lambda light chains verified gene/locus organisation and showed that no additional L chain-like genes participate in B-cell development.

In a further embodiment of the invention, the κ light chain locus of the mouse may be functionally silenced. Mice with complete L chain knock-out (KO), i.e. kappa and lambda locus silenced by gene targeting, showed a block in B-cell development at the stage when L chain expression should have been completed. These mice still produce or express μ H chain. Indeed it is expected that they produce a heavy chain antibody repertoire. There is extensive commercial interest in such mice because 1) they are the first mouse strain with silenced lambda locus and 2) by crossing with existing strains they would allow to produce mice that do not express any form of mouse H or L chain.

In a further embodiment of the invention, the heavy chain locus of the mouse may be silenced by a method of gene targeting (knock-out).

The λ, κ and heavy chain loci of the mouse may be been knocked out or silenced.

In yet a further embodiment, the mouse may carry at least one transgene which comprises one or more heavy genes or loci and/or a light chain genes or loci from a heterologous species. The mouse may produce heavy chain only antibodies of the heterologous species. The heterologous species may be human.

In a further aspect of the invention, there is provided the use of a mouse as defined above to produce antibodies. The antibodies may be produced through immunisation procedures. In a preferred embodiment, the antibodies are human.

Also provided according to the present invention is a heavy chain only antibody produced in a mouse. The antibody may have heavy chains that are either single or polymerised (dimer, trimer, etc.).

Yet further provided is an antibody produced from mice as defined above.

The antibody of the invention may be monoclonal. The antibody may be human.

In another aspect of the invention, there is provided a library of VH (variable heavy chain) domains obtained from DNA of lymphocytes from one or more mice as defined above.

Also provided is a method of producing a mouse in which the λ light chain locus is functionally silenced, comprising the step of deleting at least the constant region genes C1, C2 and C3 of the λ light chain locus. The C2-C4 loci and C3-C1 loci may be deleted simultaneously or sequentially. In one embodiment, the targeting constructs shown in FIG. 1 and described below are used.

In a further aspect of the invention there is provided one or more targeting constructs for producing a mouse in which the λ light chain locus is functionally silenced. The targeting construct(s) may be as shown in FIG. 1 and/or substantially as described below with reference to FIG. 1.

Also provided according to the invention is a mouse in which the λ light chain locus is functionally silenced, with a deletion of a λ light chain gene or genes selected from the following part of the λ locus region:
  (a) C3-C1;
  (b) C2;
  (c) C2-C1 (i.e. C2-C4-C3-C1).

BRIEF DESCRIPTION OF THE DRAWINGS

The invention will be further described in the Experimental section below with reference to the accompanying figures, of which:

FIG. 1A, The locus is ~200 kb with ~2 sets of J-C genes (J2-C2-J4-C4 and J3-C3-J1-C1) separated ~110 kb. Two V genes, V2 and Vx, are located ~75 kb and ~56 kb upstream of C2, respectively, and V1 is located ~20 kb upstream of C3. Targeted integration of C3-C1 inserts $^{tk}$Neo-loxP into C1 and loxP 3' of J3, this allows deletion of C3, J1 and 5'C1. The C2-C4 targeting construct inserts loxP$^{2k}$Neo into C2. Both targeting constructs disable all functional C genes. Upon Cre mediated deletion the region between C2 and C1 is removed. FIG. 1B, Analysis of targeted integration and Cre-mediated deletion. Southern blot of normal mouse DNA (NM), ES cell DNA from clones with homologous integration in C3-C1 (ES3.1) and C2-C4 (ES2.4), and deletion of C3-C1 (ES3.1Δ$^{+/-}$ and 3.1Δ$^{-/-}$) with digests and probes (A, B, C, D) indicated. PCR analysis of tail DNA identified the configuration of the Igλ locus before and after Cre deletion. Oligonucleotides (1-6; see below) are indicated by arrows and resulting PCR bands are the product of used oligo combinations indicated by shading. Restriction sites used for the analysis are B, BamHI; H, HindIII; R, EcoRI; S, SacI; X, XhoI; Xb, XbaI;

FIG. 3A, cytoplasmic and, separately, surface staining with FITC-coupled anti-u. FIG. 3B, separation of B-cells according to their size;

EXPERIMENTAL

Figure 1A:
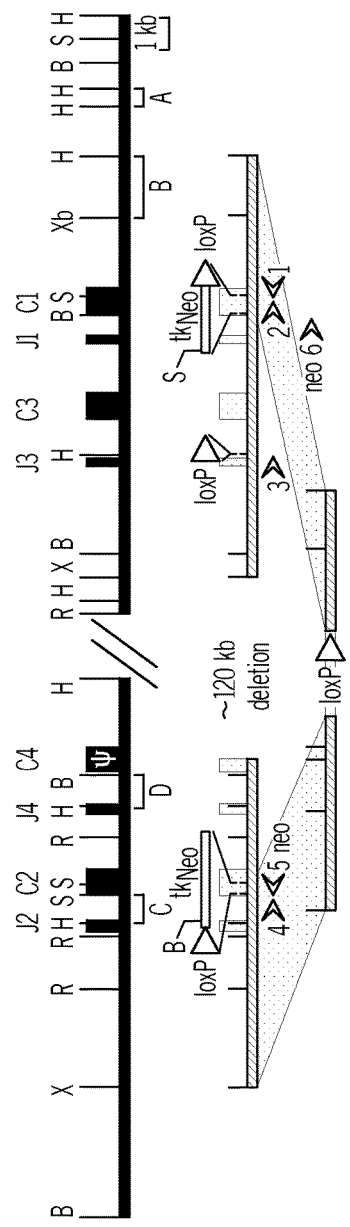
FIGS. 1A and 1B Show targeted integration and deletion of the mouse λ L chain locus.

Here we show that mice with silenced L chain loci are immunodeficient. They do not produce B-1 or B-2 cells in the periphery and B-cell development is compromised at the immature B-cell stage with a complete block at the stage of differentiation when L chain rearrangement should have been completed.

To analyse the importance of light (L) chain expression for antibody development mutant mice with targeted deletion of the Igλ locus were generated and crossed with mice carrying a non-functional Igκ locus. Successive silencing of Cλ genes in a κ$^{-/-}$ background showed a reduction in mature B-cell levels and animals with silenced L chain genes, i.e. λ$^{-/-}$ κ$^{-/-}$ mice, do not express Ig polypeptides. Their spleens are devoid of B-cells and neither peritoneal B-1 nor B-2 cells are present whilst T-cell numbers remain normal. Bone marrow pro and pre B-cells are only slightly reduced and levels of CD25$^+$ large and small pre B-II cells are largely retained. In λ$^{-/-}$κ$^{-/-}$ mice B-cell development appears to be essentially uncompromised up to the immature stage. However, a complete block is apparent when L chain rearrangement, resulting in surface IgM expression, should be completed. The lack of L chain prevents BCR association and L chain function cannot be substituted (e.g. by surrogate light chain). Is was unexpected that the lack of L chain had no profound effect on precursor cell development, such as accumulation of pre B-II cells at the pre B- to immature B-cell transition stage.

Materials and Methods

Targeting Constructs.

A phage λ library derived from ES cell DNA, a kind gift from A. Smith and T. Rabbitts (Laboratory of Molecular Biology, MRC, Cambridge, UK), was hybridised with a Vλ and Cλ probe (clone #505 kindly provided by M. Neuberger, MRC, UK) which identified several clones containing Vλ and, separately, Cλ genes. Part of the C2-C4 and C3-C1 regions were subcloned in pUC19 to assemble the constructs and to obtain gene probes. This allowed blunt end insertion of loxP from pGEM-30 (Gu, H. et al., 1993, Cell 73: 1155-1164) in the HindIII site 3' of J3, loxP insertion in $^{tk}$Neo (Stratagene, La Jolla, Calif.) and blunt end insertion of $^{tk}$Neo-loxP into Cλ1, and loxP-$^{tk}$Neo, derived from pGH-1 (pGEM-30 and pGH-1 were a kind gift from H. Gu, Institute for Genetics, University of Cologne, Germany), into Cλ2 (see FIG. 1a). The ~14 kb C3-C1 targeting construct was obtained by XhoI and HindIII digest and the ~13 kb C2-C4 targeting construct was obtained by XhoI excision in the internal and polylinker site. Restriction sites for integration of $^{tk}$Neo (SacI and BamHI) or loxP (HindIII) in the targeting constructs were not maintained.

Analysis of Homologous Integration.

Methods used for electroporation of targeting constructs and ES cell selection have been described (Zou, X. et al., 1995, supra). The C3-C1 construct was integrated in HM-1 (Selfridge, J. et al., 1992, Somat. Cell. Mol. Genet. 18: 325-336) and C2-C4 was integrated in λES3.1Δ-5 ES cells. Targeting of C3-C1 was identified with a 0.4 kb HindIII fragment (probe A, all probes are marked in FIG. 1a) and SacI digest of ES cell DNA, and verified with a 2 kb XbaI-HindIII fragment (probe B) and SacI, HindIII and BamHI digests which also allowed identification of C3-C1 Cre-loxP deletion. Homologous integration in C2-C4 was identified with a 0.7 kb HindIII-XbaI fragment (probe C, the XbaI site is immediately 5' of SacI) and a 1.2 kb HindIII-BamHI fragment (probe D), and HindIII and BamHI digests of ES cell DNA. To obtain deletion of the λ locus the Cre plasmid pBS185 (GIBCO, #10347-011) was transiently integrated by electroporation (Zou, X. et al., 1995, supra). Clones were tested by PCR using the following oligonucleotides (arrow 1-6 in FIG. 1a):

```
                                          (SEQ ID NO: 1)
C1rev     5'-GCCTTTCCCATGCTCTTGCTGTCAGGG-3' (<1);

(SEQ ID NO: 2)
C1for     5'-CCAAGTCTTCGCCATCAGTCACCC-3' (2>);

(SEQ ID NO: 3)
3'J3for   5'-CCCAGGTGCTTGCCCCACAGGTTTAGG-3' (3>);

(SEQ ID NO: 4)
5'C2for   5'-GGAGATCAGGAATGAGGGACAAAC-3' (4>);

(SEQ ID NO: 5)
3' ᵗᵏNeorev 5'-CTCGACGGATCCGTCGAGGAATTCC-3'

(<5 neo);
and
                                          (SEQ ID NO: 6)
ᵗᵏNeofor  5'-ATGGCCGATCCCATATTGGCTGCAGGG-3'

(neo 6>).
```

Oligos 1-2 and separately, 4-5 identified construct integration whilst the combination of oligos 1-3 and 1-4 identified partial or complete C gene deletion. PCR reactions were performed under the following conditions: two initial cycles of 45 sec at 97° C., 30 sec at 60° C. and 60 sec at 72° C. followed by 30 cycles with 30 sec at 94° C., 30 sec at 60° C. and 60 sec at 72° C., and 10 min at 72° C. to complete the reaction.

Derivation of Mice.

Chimeric mice and germline transmission was obtained as described (Hogan, B. et al., 1994a, In: Manipulating the mouse embryo, a laboratory manual, Cold Spring Harbor Laboratory Press, Cold Spring Harbor, p 253-289. λ1.3 mice, in a 129/Ola x Balb/c background, were mated with 129/Ola mice for 5 generations and crossed with Cre mice and each other to obtain homozygous λ1.3$^{-/-}$ mice. For the derivation of ES cells, blastocysts were collected and cultured on mitomycin-C treated feeder cells (Hogan, B. et al., 1994b, In: Manipulating the mouse embryo, a laboratory manual, Cold Spring Harbor Laboratory Press, Cold Spring Harbor, p 217-251). Several ES cell lines were obtained and λES3.1Δ-5, a female line, was used for integration of the C2-C4 targeting construct.

For the derivation of transgenic mice expressing Cre-protein ubiquitously, the Cre plasmid pBS185 was linearised with ScaI and purified using a DNA purification kit (Qiagen #28304). DNA was microinjected into the male pronucleus of F1 embryos (CBA×C57Bl/6) according to standard methods (Hogan, B. et al., 1994b, supra) and several founders were produced, two of which showed a high gene/locus deletion rate when crossed with loxP mice.

Flow Cytometry Analysis.

For the analysis of B cell populations by flow cytometry cells from the different tissues were prepared and stained with various combinations of differently labelled antibodies against cell surface markers (see FIG. 2): these were for bone marrow cells PE-conjugated anti-mouse c-kit (CD117) (09995B; PharMingen), Phycoerythrin (PE)- or allophycocyanin (APC)-conjugated anti-mouse CD45R (B220) (01125A, 01129A; PharMingen, San Diego, Calif.), Biotin-conjugated anti-mouse CD25 (01092A; PharMingen), FITC-conjugated monoclonal rat anti-mouse IgM (μ chain specific, 04-6811; Zymed) and/or Biotin-conjugated anti-mouse CD43 (01602D; PharMingen); for spleen cells PE- or APC-conjugated anti-mouse CD45R (B220) (01125A, 01129A; PharMingen), Biotin-conjugated anti-mouse IgM (μ chain specific, 02082D; PharMingen), FITC-conjugated anti-mouse IgD (02214D; PharMingen), Biotin or FITC conjugated anti-mouse Igλ (02172D, 02174D; PharMingen) and/or PE-conjugated anti-mouse Igκ (559940, PharMingen); and for peritoneal cells PE-conjugated anti-mouse CD5 (Ly-1) (01035A; PharMingen) and APC-conjugated anti-mouse CD45R (B220) (01125A, 01129A; PharMingen).

For cytoplasmic staining bone marrow B-cells were pretreated using a fix and perm cell permeabilization kit (GSA-004, Caltag) and then stained with FITC-conjugated monoclonal rat anti-mouse IgM (μ chain specific, 04-6811; Zymed), PE-conjugated anti-mouse CD45R (B220) (01125A, 01129A; PharMingen) and Biotin-conjugated anti-mouse CD25 (01092A; PharMingen) according to the manufacturer's protocol. Binding of biotinylated antibody was developed with streptavidin-Quantum Red (S2899; Sigma) or strepavidin-Tri-color (SA1006, Caltag, Burlingame).

Protein Analysis.

Serum antibodies were identified by ELISA as described (Zou, X. et al., 1995, supra). For separation on acrylamide gels digitonin lysates of bone marrow cells (Bell, S. E. et al., 1994, EMBO J. 13(4): 816-26) and, separately, serum was incubated for 1 h at 4° C. with anti-mouse IgM (μ chain specific, The Binding Site, Birmingham, UK) coupled to CNBr-activated Sepharose 4B (Pharmacia LKB, Uppsala, Sweden) as described (March, S. C et al., 1974, Anal. Biochem. 60: 149-152). Samples were fractionated on 4-15% precast gels (161-1104, Bio-Rad, Hemel Hempstead, UK) and, after transfer to nitrocellulose membranes, incubated with biotinylated anti-mouse μ (B-9265, Sigma) for 1 h at RT and then placed in streptavidin biotinylated horseradish peroxidase (HRP) solution (RPN 1051, Amersham) for 30 minutes on a rocker. Bands were visualised with SuperSignal West Pico chemiluminescent substrate (34080, Pierce, Ill.).

Results

Silencing of the Mouse λ L Chain Locus.

Figure 1B:
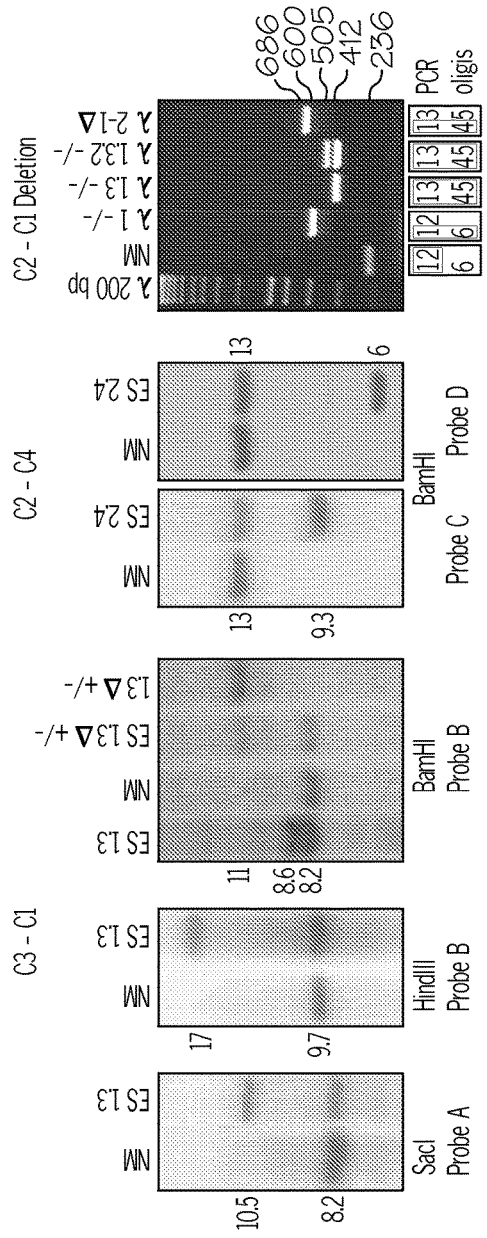

To investigate B-cell development without L chain we produced mice with a deleted Igλ locus. The $\lambda^{-/-}$ mice were crossed with animals carrying a non-functional Igκ locus, $\kappa^{-/-}$ mice, also obtained by gene targeting (Zou, X. et al., 1995, supra). The mouse λ L chain locus contains 3 V (variable) region genes, 4 J (joining) segments and 4 C (constant) region genes which can independently rearrange and express 3 different λ L chains. C4 has not found to be expressed. Silencing of the λ locus was carried out in 4 successive steps by introduction of 3 loxP sequences and targeting of C1 and C2 (FIG. 1a). Introduction of the C3-C1 targeting construct silenced C1 and germline transmission mice were produced which, upon mating with ubiquitous Cre expressers, had C3-C1 deleted on both alleles. Such mice, bred into the 129/Ola background, were used for the derivation of embryonic stem (ES) cells which allowed homologous integration and silencing of C2. Germline transmission mice were obtained and bred with the Cre expressers and each other which resulted in homozygous animals with a C2 to C1 deletion of ~120 kb. Analysis of ES cells and mice by Southern blot and PCR, with representative examples shown in FIG. 1b, identified homologous integration and locus deletion and resulted in separate animals with the following genes silenced: a) $\lambda C1^{-/-}$ (mouse 130=ES1.3), b) $\lambda C1^{-/-}$ and $\lambda C3^{-/-}$ (mouse 1.3=ES1.3Δ), c) $\lambda C1^{-/-}$, $\lambda C2^{-/-}$ and $\lambda C3^{-/-}$ (mouse 50=ES2.4) and c) deletion of $\lambda C1^{-/-}$, $\lambda C3^{-/-}$ and $\lambda C4^{-/-}$ (mouse 1.3-2.44). These mouse strains were crossed into the $\kappa^{-/-}$ background and termed according to their silenced or deleted (Δ) C genes: $\lambda 1^{-/-}\kappa^{-/-}$, $\lambda 1.3^{-/-}\kappa^{-/-}$, $\lambda 1.3.2^{-/-}\kappa^{-/-}$ and $\lambda 1-2\Delta^{-/-}\kappa^{-/-}$. Deletion of the λ locus was verified by sequencing of the 686 bp PCR fragment shown in FIG. 1b which contained the 3' J2 and 3' C1 region separated by loxP.

B-Cell Reduction Upon Cλ Gene Removal.

Figure 2A:
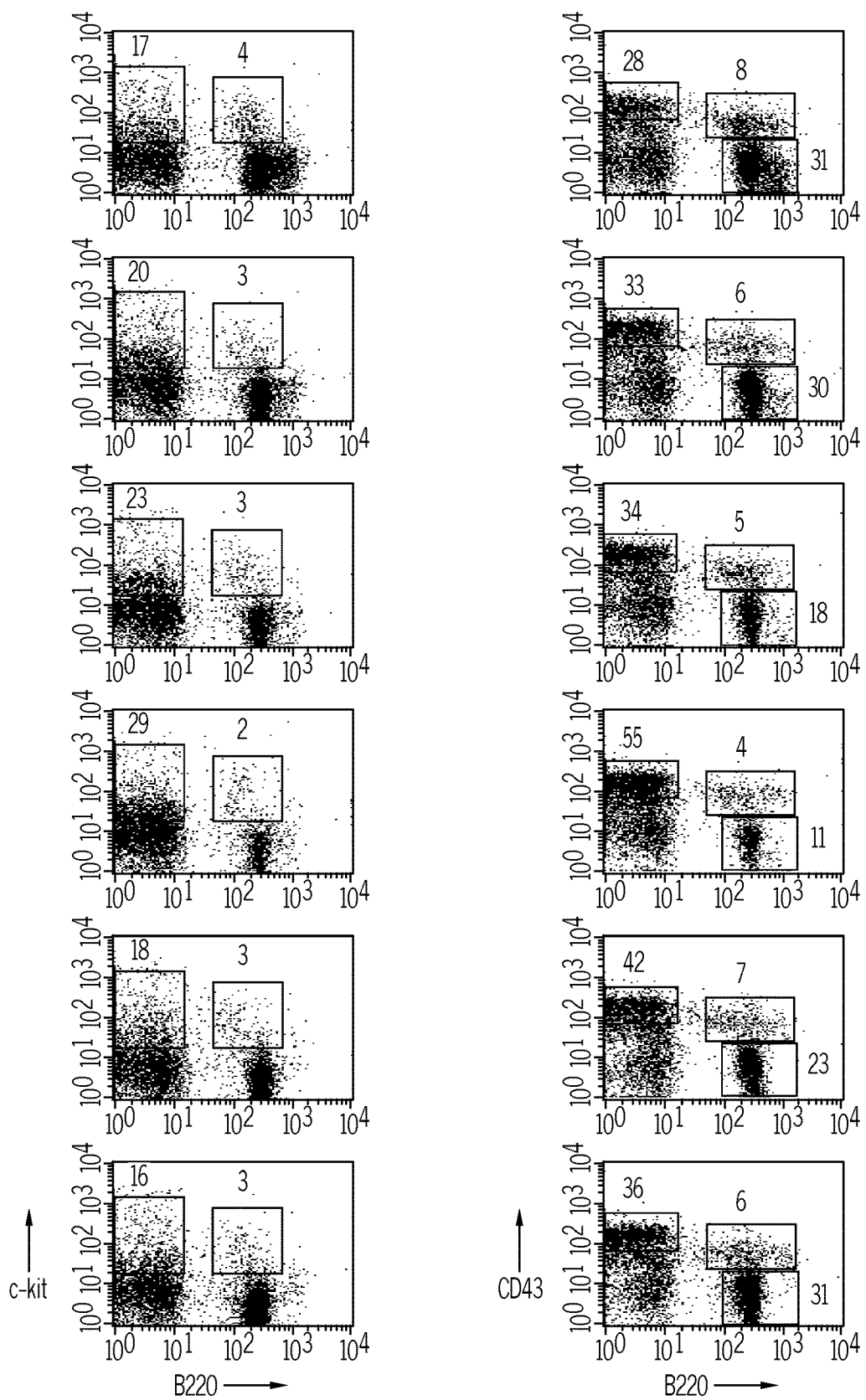
FIGS. 2A and 2B Show flow cytometry analysis of FIG. 2A, bone marrow and FIG. 2B, splenic B-cell populations from normal (NM), κ$^{-/-}$, λ1$^{-/-}$κ$^{-/-}$, λ1.3$^{-/-}$κ$^{-/-}$, λ1.3.2$^{-/-}$κ$^{-/-}$ and λ1-2Δ$^{-/-}$κ$^{-/-}$ mice. The profiles are representative for results obtained for at least 5 mice per group and show staining of gated bone marrow lymphocytes with PE-conjugated c-kit, biotin-conjugated anti-mouse CD43, biotin-conjugated anti-mouse CD25 or biotin-conjugated anti-IgM in combination with PE- or APC-conjugated anti-B220. Spleen cells were stained with biotin-conjugated anti-IgM, FITC-conjugated anti-IgD, biotin- or FITC-conjugated anti-λ and/or PE-conjugated anti-κ and APC-conjugated anti-B220 for setting the B-lymphocyte gate.
Figure 2A:
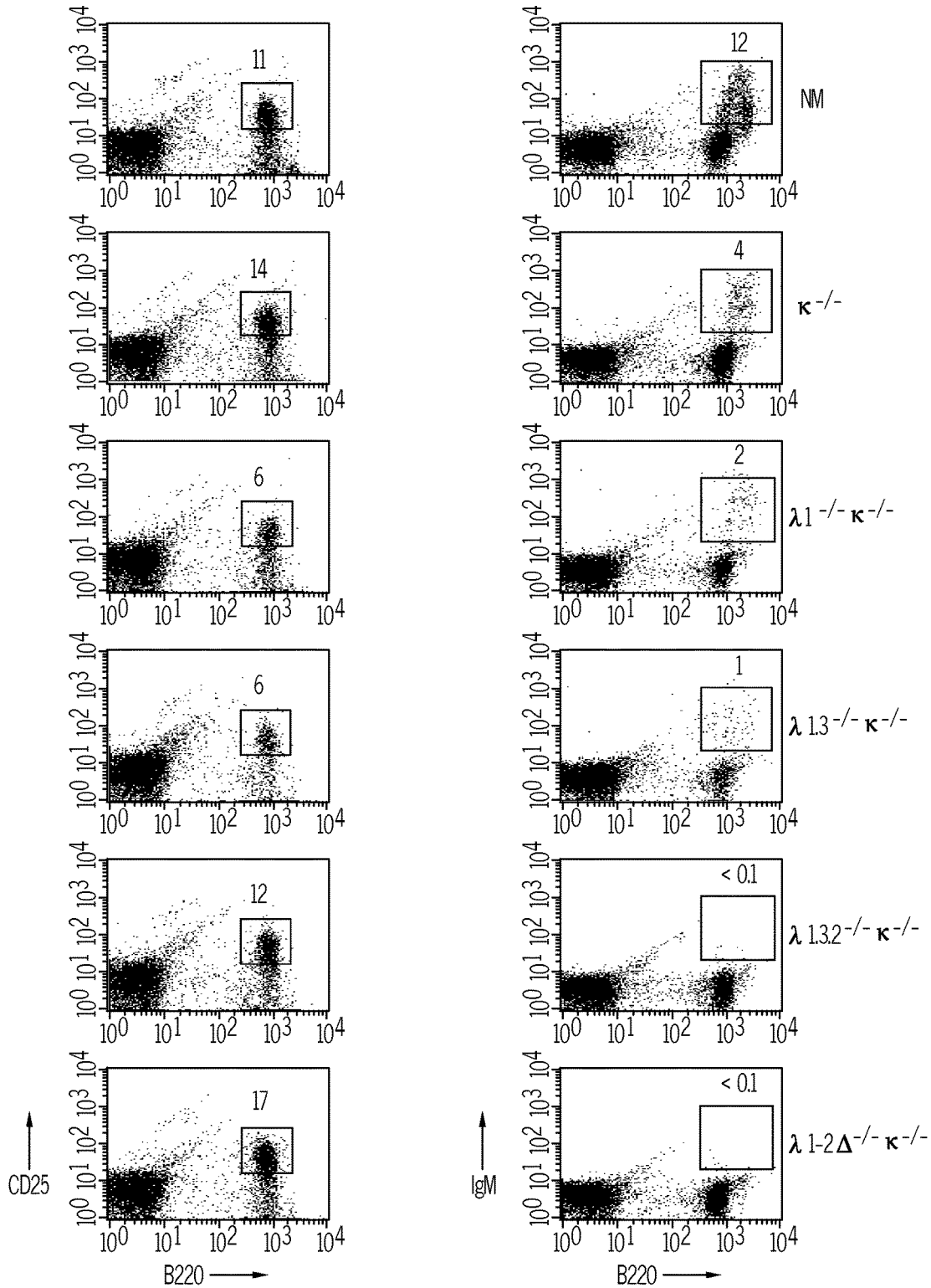
Figure 2B:
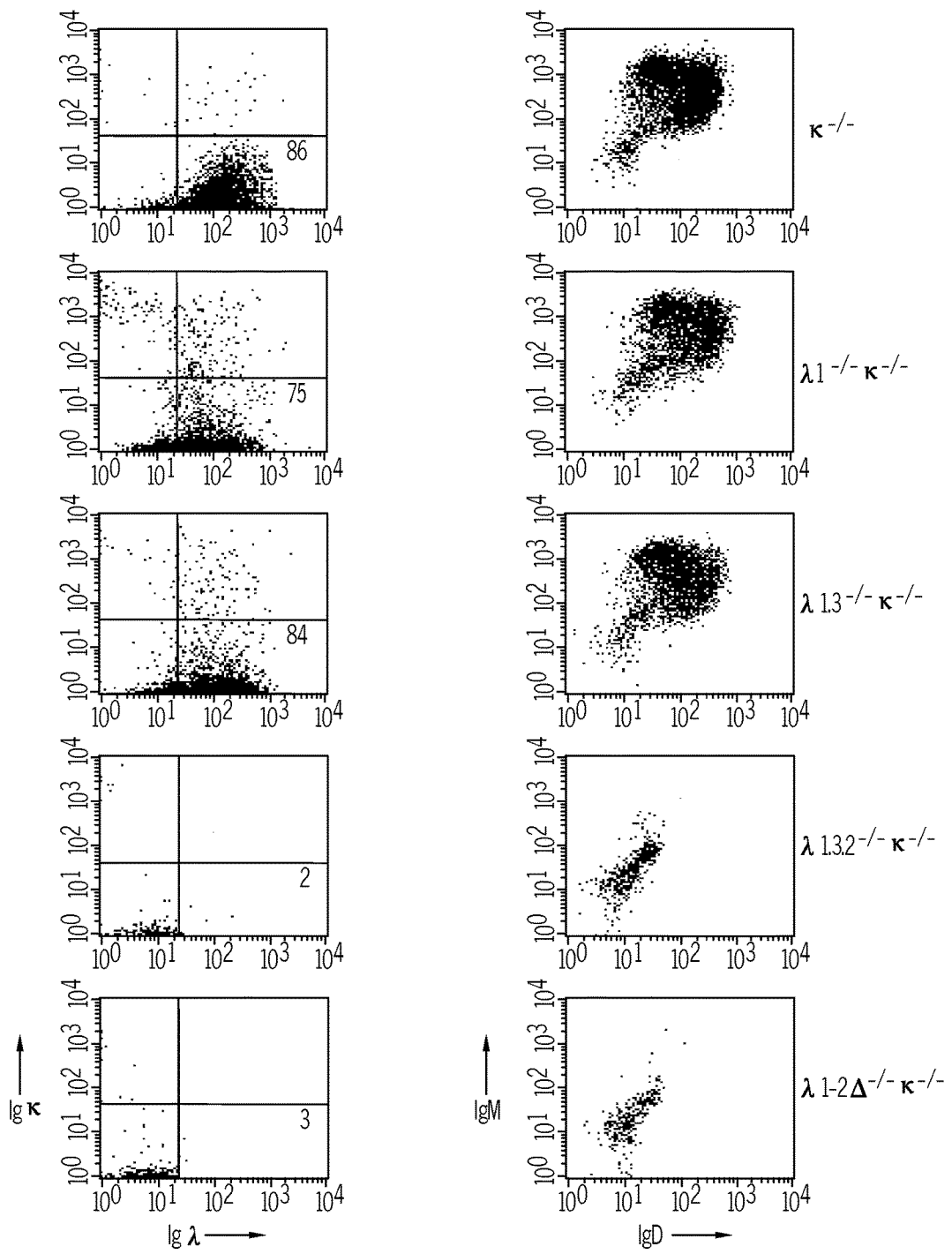

Mice with individually silenced Cλ genes in the $\kappa^{-/-}$ background showed significantly reduced numbers of mature IgM$^+$ B-cells compared to normal mice kept in the same pathogen-free conditions (Table 1). Serum antibodies in $\lambda 1^{-/-}\kappa^{-/-}$ and $\lambda 1.3^{-/-}\kappa^{-/-}$ were also reduced but comparable to those in $\kappa^{-/-}$ mice (Zou, X. et al., 1995, supra). Unexpectedly $\lambda 1.3.2^{-/-}\kappa$ and $\lambda 1-2\Delta^{-/-}\kappa^{-/-}$ mice derived from heterozygous females or foster mothers had significant antibody titers in serum still detectable by ELISA 6 weeks after weening. However, serum analyses from such mice older than 3 months showed that no antibodies remain (data not shown). The lack of serum Ig in $\lambda 1.3.2^{-/-}\kappa^{-/-}$ mice confirms that Cλ4 must be a pseudogene and that the remaining Vλ genes cannot be expressed using an as yet unknown C gene. The reduction of B-cell levels in bone marrow and spleen at each successive silencing step is shown in FIG. 2 and Table 1. In the bone marrow pro and pre B-cell development appears to be little affected by the loss of L chain expression and the levels of c-kit$^+$, CD43$^+$ and CD25$^+$ B-cells are quite similar in the KO strains and compared to normal mice (FIG. 2a). However, at the stage when L chain rearrangement should have been completed normal development is blocked and immature B-cells fail to express surface IgM. Interestingly, a reduction in the number of cells expressing surface IgM is clearly visible and, compared to the 12% of IgM$^+$ B220$^+$ lymphocytes in normal mouse bone marrow, 4% are found in $\kappa^{-/-}$ mice, 2% in $\lambda 1^{-/-}\kappa^{-/-}$, 1% in $\lambda 1.3^{-/-}\kappa^{-/-}$ and essentially none in $\lambda 1.3.2^{-/-}\kappa$ and $\lambda 1-2\Delta^{-/-}\kappa^{-/-}$ mice. In the spleen the levels of Ig$^+$ B-cells in $\lambda 1^{-/-}\kappa^{-/-}$ and $\lambda 1.3^{-/-}\kappa^{-/-}$ mice are similar to those in $\kappa^{-/-}$ mice whilst in $\lambda 1.3.2^{-/-}\kappa^{-/-}$ and $\lambda 1-2\Delta^{-/-}\kappa^{-/-}$ mice only background staining remains (FIG. 2b).

Figure 3A:
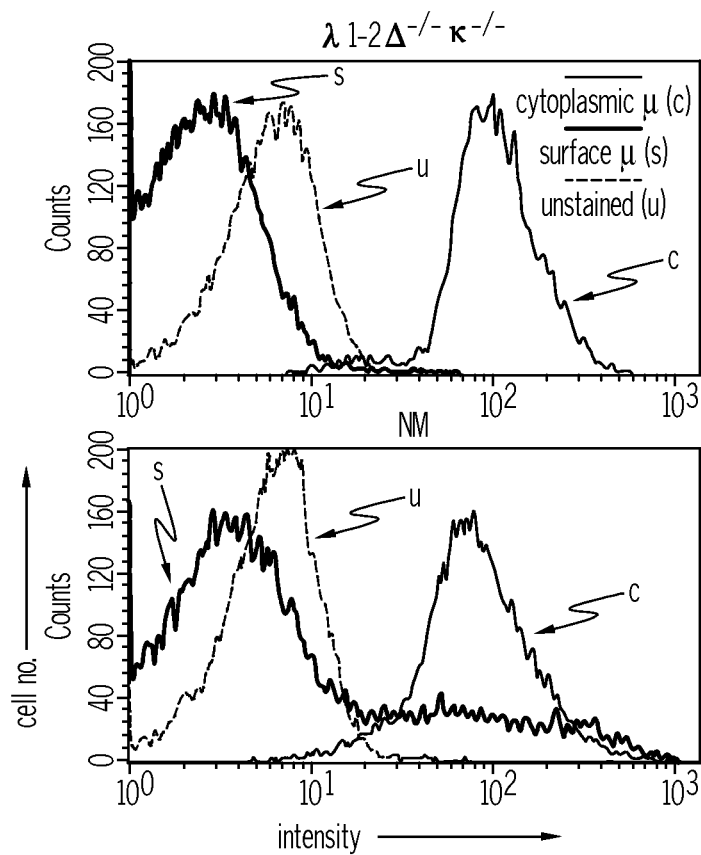
FIGS. 3A and 3B Show cytoplasmic and surface staining of CD25$^+$ bone marrow B-cells from λ1-2Δ$^{-/-}$κ$^{-/-}$ and normal (NM) mice.
Figure 3B:
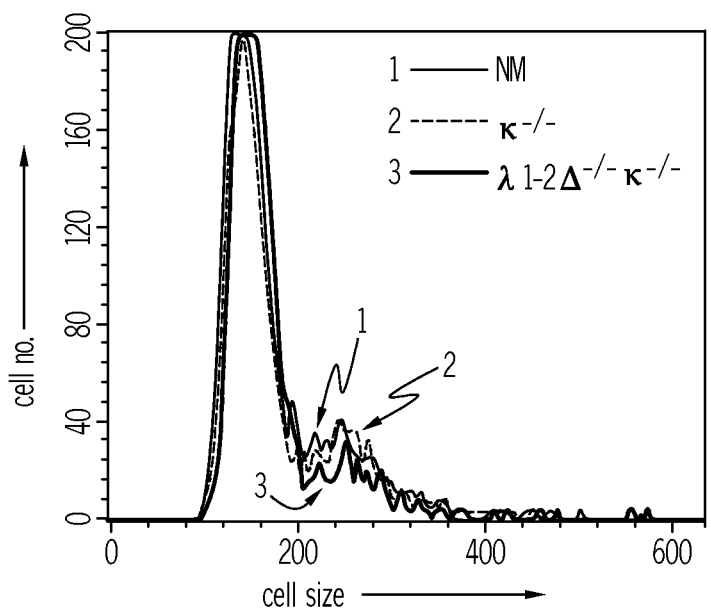
Figure 4:
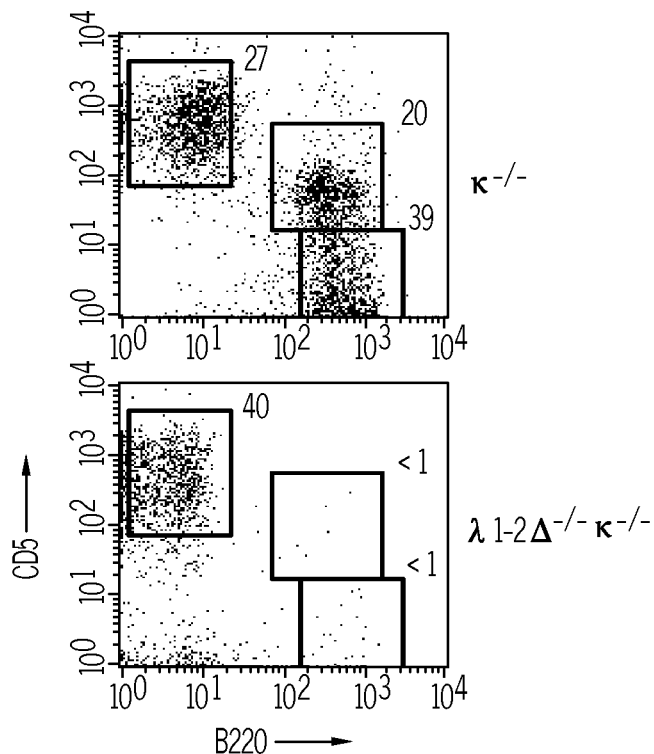
FIG. 4 Shows flow cytometry analysis of B- and T-cells in the peritoneum of κ$^{-/-}$ and λ1-2Δ$^{-/-}$κ$^{-/-}$ mice. Cells were stained with PE-conjugated anti-CD5 and APC-conjugated anti-B220.
Figure 5:
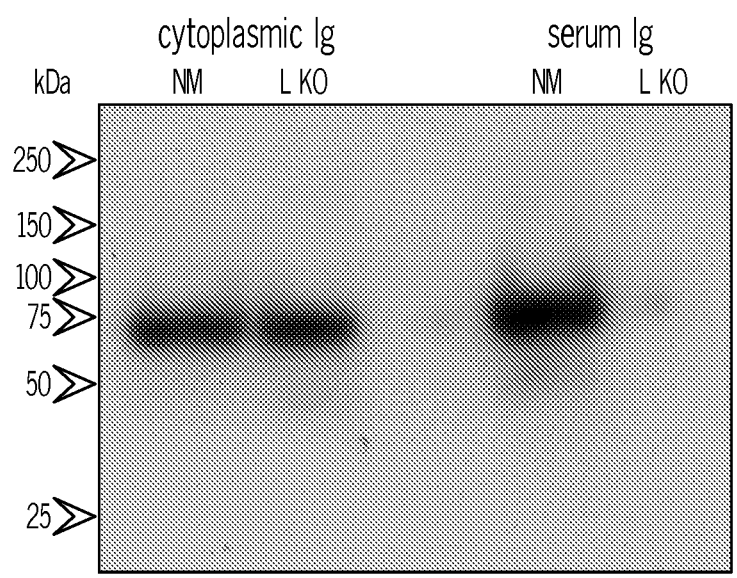
FIG. 5 Shows gel separation of cytoplasmic and serum antibodies from λ1-2Δ$^{-/-}$κ$^{-/-}$ (L KO) and normal (NM) mice captured with anti-μ.

To evaluate if B220$^+$ B-cells in the bone marrow do accumulate μ H chain in the cytoplasm and if these cells migrate to secondary lymphoid organs we stained for cytoplasmic IgM. As shown in FIG. 3a CD25$^+$ bone marrow B-cells from $\lambda 1-2\Delta^{-/-}\kappa^{-/-}$ mice do indeed stain for cytoplasmic μ H chain but show no staining for surface IgM. Indeed the levels of CD25$^+$ B-cells and their size distribution is very similar in normal and L KO mice (FIG. 3b). However, migration of these cells to, for example, the peritoneum is not taking place and FIG. 4 shows that essentially no B-cells exist in secondary lymphoid organs. We wondered if the identified μ H chain in the cytoplasm of B-cells from $\lambda 1-2\Delta^{-/-}\kappa^{-/-}$ mice is of the same size or molecular weight as conventional μ H chain. Cell lysis using digitonin and capturing bound or unbound μ H chain, analysed on polyacrylamide gels (FIG. 5), showed no size difference of the μ H chain produced in the cytoplasm of normal or L chain silenced mice. However, as also shown in FIG. 5 serum Ig is not produced by these mice. This re-emphasises that B-cell development and μ H chain expression up to the stage when L chains are expressed appears to be largely unaffected in L chain KO mice. Furthermore, the lack of L chain prevents the release of μ H chain from the cell which prevents Ig secretion.

Block in Development at the Immature B-Cell Stage.

Silencing of the λ L chain genes in a $\kappa^{-/-}$ background showed that no surface or secreted Ig is produced and that the resulting block in B-cell development is established at the pre B-II to immature transition phase. At this stage CD25 expression is revoked, the pre BCR is replaced by the BCR, surrogate L chain is no longer expressed and κ or λ L chain rearrangement is completed with successful expression that allows μ H chain association. After several divisions large CD25$^+$ pre B-II cells differentiate into small CD25$^+$ resting pre B-II cells which are in the process of rearranging their L chain genes. As can be seen in FIG. 2a the number of CD25$^+$ B220$^+$ cells at the stage immediately before the developmental block is by and large very similar. As successful L chain rearrangement is prevented or impaired in the mutant mice we wondered if this block in development alters the ratio of large and small CD25$^+$ cells. In FIG. 3b the number of CD25$^+$ gated bone marrow cells from age-matched normal, $\kappa^{-/-}$ and $\lambda 1-2\Delta^{-/-}\kappa^{-/-}$ mice is plotted against cell size. The comparison shows slight variations as expected but no major differences in the large and small pre B-II cell populations. This concludes that the failure to express L chain initiates a complete block in development at the immature B-cell stage when surface IgM should be expressed. In addition no immature B-cells accumulate before the event.

This block in development with no apparent recovery impedes surface IgM expression and subsequent cell migration. As shown in Table 1 the number of spleen cells in $\lambda 1.3.2^{-/-}\kappa^{-/-}$ and $\lambda 1\text{-}2\Delta^{-/-}\kappa^{-/-}$ mice is significantly reduced. A complete lack of mature B-cells is also found in the peritoneal cavity with no B220$^+$ and B220$^+$CD5$^+$ cells (FIG. 4). This lack of B-1 and B-2 cells appears to have no effect on T-cell levels which are maintained.

DISCUSSION

Our experiments show that B-cell development is aborted in L chain deletion mice at the pre B-II to immature B-cell transition stage when surface receptor expression should have been accomplished. This complete block in development prevents B-cell maturation and the mouse is immunodeficient regarding antibody expressing B-cells. The surrogate L chain encoded by VpreB and $\lambda 5$ does not sustain B-cell development and with the failure to express L chain polypeptides B-cell differentiation ceases exactly at the stage when L chain rearrangement should have been completed. This re-emphasises the importance of L chain for immune development and that, at least in the mouse, there is no gene or rescue event that can compensate L chain deficiency.

B-cell development in the mouse has been extensively studied by gene targeting and in one of the early experiments a μ transmembrane exon was rendered non-functional which prevented surface IgM expression. This μMT KO caused a block in development, leading to the accumulation of pre B-I and the disappearance of pre B-II cells. With the lack of surface IgM expression no proliferation or differentiation into immature or mature B-cells was obtained, however, DNA rearrangement was maintained. Indeed the μMT mice do rearrange H and L chain genes whilst H chain KO mice without J segments maintain L chain rearrangement. This is in agreement with the results of our $\lambda^{-/-}\kappa^{-/-}$ mice which show H chain rearrangement and cytoplasmic Igμ expression which reiterates that H and L chain rearrangement and expression are independent events. The critical importance of the BCR in signalling and normal progression of development through the different B-cell maturation stages was further analysed by gene targeting of individual BCR components. The results showed that silencing of some genes, such as the Igκ L chain locus, had a moderate effect on B-cell development and is well tolerated whilst the function of other genes, such as Cu or Igβ, is essential and blocks any progress in development. The block in B-cell development was frequently accompanied by the accumulation of cells prior to the stage of differentiation when the silenced gene should be active. Surprisingly this is not seen at any pro or pre B-cell stage in the $\lambda^{-/-}\kappa^{-/-}$ mice and the numbers of CD25$^+$ large and small B-cells immediately prior to the block in development are similar to those found in a normal mouse. A reason for this may be that the cells entering the pre B-II stage and those being apoptosed, perhaps half of the CD25$^+$ cells generated in the bone marrow die without maturing into IgM$^+$ B-cells, allow to maintain fairly constant cell levels.

The importance of L chain expression has been studied in RAG-1 and RAG-2 KO mice where B-cell development is arrested at the B220$^+$CD43$^+$ pro B-cell stage. Upon introduction of a rearranged H chain Igμ was expressed in the cytoplasm which is in agreement with the observation that L chain facilitates dissociation of H chain binding protein and transport to the cell surface. However, to direct the development of a B-lineage cell population in RAG$^{-/-}$ mice both rearranged H and L chain genes had to be introduced. In the bone marrow of RAG-1$^{-/-}\lambda 5^{-/-}$ mice carrying a rearranged H chain transition from pro B to pre B-cell and surface IgM expression was only seen when either $\lambda 5$ or a rearranged L chain was introduced. Nussenzweig and colleagues argued that when neither $\lambda 5$ nor conventional L chain are expressed B cell development cannot proceed past the pro-B-cell stage. This is not seen in our mice with silenced $\lambda$ and $\kappa$ light chain locus where B-cell development allows heavy chain expression and developmental progress to the pre B-II cell stage. This application claims the benefit of priority to GB 0115256.0 which was filed on Jun. 21, 2001.

TABLE 1

Cell numbers in spleen and bone marrow of normal, $\kappa^{-/-}$ and C $\lambda$ deletion mice.

| Organ | NM | $\kappa^{-/-}$ | $\lambda 1^{-/-}\kappa^{-/-}$ | $\lambda 1.3^{-/-}\kappa^{-/-}$ | $\lambda 1.3.2^{-/-}\kappa^{-/-}$ | $\lambda 1\text{-}2\Delta^{-/-}\kappa^{-/-}$ |
|---|---|---|---|---|---|---|
| Bone Marrow | | | | | | |
| total cell no. × 10$^6$* | 18 | 14 | 9 | 6 | 2 | 1 |
| c-kit$^+$, B220$^+$ pro B-cells | 0.52 | 0.24 | 0.14 | 0.08 | 0.04 | 0.02 |
| B220$^+$, CD43$^+$ pro/pre B-cells | 0.95 | 0.51 | 0.29 | 0.16 | 0.08 | 0.04 |
| B220$^+$, CD25$^+$ immat. B-cells | 1.32 | 1.26 | 0.36 | 0.21 | 0.14 | 0.10 |
| B220$^+$, IgM$^+$ immat./mat. B-cells | 1.34 | 0.33 | 0.10 | 0.05 | 0.01 | 0.10 |
| B220$^+$ B-cells | 3.89 | 2.61 | 1.00 | 0.48 | 0.27 | 0.18 |
| IgM$^+$ B-cells | | | | | | |
| Spleen | | | | | | |
| total cell no. × 10$^6$ | 38 | 42 | 28 | 32 | 31 | 24 |
| B220$^+$ | 10.40 | 7.42 | 3.62 | 4.31 | 0.67 | 0.39 |
| IgM$^+$ | 9.69 | 6.60 | 3.10 | 3.74 | 0.03 | 0.02 |
| IgD$^+$ | 7.81 | 3.10 | 1.18 | 1.51 | <0.01 | <0.01 |
| IgL$^+$ | | | | | | |

Cells were stained with relevant antibodies for the listed features (see Materials and Methods) and analysed by Total cell numbers were determined by Trypan blue staining.
*Cells were from one femur.

The invention claimed is:

1. A knock-out mouse comprising one or more deletions that functionally silence the immunoglobulin lambda light chain locus of the knock-out mouse, wherein the one or more deletions that functionally silence the immunoglobulin lambda light chain locus of the knock-out mouse consist of:
   (a) a deletion of lambda light chain genes C2 and C3-C1; or
   (b) a deletion of lambda light chain genes C2, C4, C3 and C1,
   wherein the lambda light chain locus is not deleted completely.

2. The knock-out mouse according to claim 1, wherein the mouse immunoglobulin κ light chain locus is functionally silenced by targeted integration of a selectable marker gene in Cκ or targeted deletion of Cκ or Jκ.

3. The knock-out mouse according to claim 1, wherein the mouse immunoglobulin heavy chain locus is functionally silenced by targeted integration of a selectable marker gene in the μ membrane exons or targeted deletion of the JH gene segments.

4. The knock-out mouse according to claim 1, wherein the knock-out mouse comprises one or more heavy and/or a light chain immunoglobulin genes or loci from a human.

5. The knock-out mouse according to claim 2, wherein the mouse immunoglobulin heavy chain locus is functionally silenced by targeted integration of a selectable marker gene in the μ membrane exons or targeted deletion of the JH gene segments.

6. A method comprising the steps of:
   (a) providing a knock-out mouse according to claim 1, wherein the mouse immunoglobulin κ light chain locus is functionally silenced by targeted integration of a selectable marker gene in Cκ or targeted removal of Cκ or Jκ and wherein the mouse immunoglobulin heavy chain locus is functionally silenced by targeted integration of a selectable marker gene in the μ membrane exons or targeted deletion of the JH gene segment; and
   (b) introducing into said knock-out mouse at least one transgene which comprises one or more immunoglobulin heavy genes or loci from a heterologous species wherein the heterologous species is human.

7. A method for making a library of VH domains comprising
   (a) providing a knock-out mouse of claim 1 wherein the mouse immunoglobulin κ light chain locus is functionally silenced by targeted integration of a selectable marker gene in Cκ or targeted removal of Cκ or Jκ and wherein the mouse immunoglobulin heavy chain locus is functionally silenced by targeted integration of a selectable marker gene in the μ membrane exons or targeted deletion of the JH gene segment;
   (b) introducing into said knock-out mouse at least one transgene which comprises one or more immunoglobulin heavy chain genes or loci from a heterologous species wherein the heterologous species is human; and
   (c) preparing a library of VH domains from DNA of lymphocytes from said knock-out mouse.

* * * * *